United States Patent [19]

Urasaki

[11] Patent Number: 4,551,508

[45] Date of Patent: Nov. 5, 1985

[54] POLYGLYCIDYL ETHERS, PROCESS FOR PRODUCTION THEREOF, AND CURED PRODUCTS THEREOF

[75] Inventor: Takanori Urasaki, Iwakuni, Japan

[73] Assignee: Agency of Industrial Science and Technology, Tokyo, Japan

[21] Appl. No.: 613,306

[22] Filed: May 23, 1984

[30] Foreign Application Priority Data

May 25, 1983 [JP] Japan .................................. 58-90621

[51] Int. Cl.[4] ............................................. C08G 59/08
[52] U.S. Cl. ...................................... 525/507; 528/88; 528/93; 528/97; 528/107; 525/503; 525/504; 525/505; 525/481
[58] Field of Search ................. 528/88, 93, 97, 107; 525/507

[56] References Cited

U.S. PATENT DOCUMENTS 3,996,185 12/1976 Barie et al. ........................... 525/507
4,368,298 1/1983 Okayama et al. .................... 525/507
4,468,508 8/1984 Ito et al. .............................. 525/507

FOREIGN PATENT DOCUMENTS 0513993 5/1976 U.S.S.R. .

*Primary Examiner*—John Kight
*Assistant Examiner*—Garnette D. Draper
*Attorney, Agent, or Firm*—Sherman & Shalloway

[57] ABSTRACT

Polyglycidyl ethers of the formula

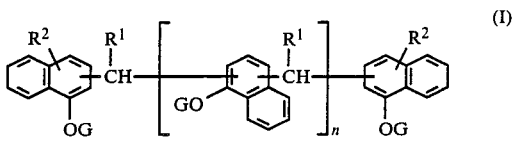 (I)

wherein:
G represents hydrogen,

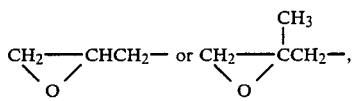

$R^1$ represents a hydrogen atom, an aliphatic, alicyclic, or aromatic hydrocarbon group, or a 5- or 6-membered oxygen or sulfur atom containing heterocyclic group which groups, other than hydrogen, may be substituted by halogen or the group —OG,
$R^2$ is hydrogen or

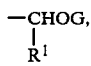

n is a positive number up to 10,
and at least two G groups in the molecule are other than hydrogen. The polyglycidyl ether is produced by condensing alpha-naphthol with an aldehyde, such as acetaldehyde, in the presence of an acid catalyst such as nitric acid, and optionally in the presence of an inert medium such as toluene, to form a novolak-type phenol which is thereafter condensed with an epihalohydrin. The polyglycidyl ethers may be cured with conventional curing agents. Composite materials containing a matrix formed from the cured polyglycidyl ether and a filler dispersed in the matrix have excellent heat resistance and low water absorption.

20 Claims, No Drawings

POLYGLYCIDYL ETHERS, PROCESS FOR PRODUCTION THEREOF, AND CURED PRODUCTS THEREOF

This invention relates to novel polyglycidyl ethers, a process for production thereof, and cured products thereof. More specifically, it relates to novel polyglycidyl ethers having alpha-naphthol as a phenol, a process for production thereof, and cured products thereof having excellent heat resistance and a low water absorption.

With regard to a polyepoxy compound having a bicyclic hydroxy aromatic compound as a phenol, a method has previously been known which comprises reacting beta, beta'-dihydroxy-dinaphthylmethane and epichlorohydrin as starting materials in the presence of sodium hydroxide to form a diepoxide represented by the following formula

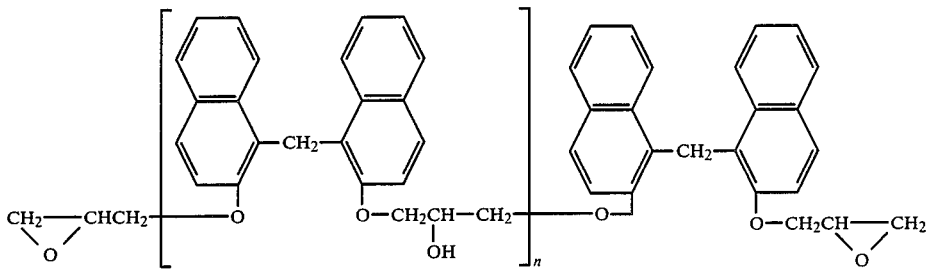

and curing the diepoxide with phthalic anhydride as a curing agent to form a cured resin [see Makromol. Chem., vol. 83, pages 226–233 (1965)]. The diepoxide above is structurally characterized by having a beta-naphthyl skeleton.

Where n is 0 in the above formula, the diepoxide is represented by the following formula.

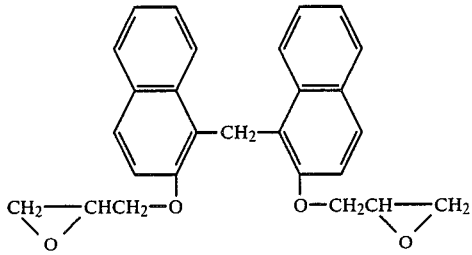

The present inventor's investigation has shown that since the diepoxide, i.e. diglycidyl ether, has a melting point of as high as 170° C. or more despite its low degree of polymerization, it has poor solubility in solvents and lends itself to difficult handling, and that curing it with a curing agent does not give a resin having good heat resistance.

U.S. Pat. No. 3,996,185 discloses a liquid impregnant for binding fibrous reinforcing material, which comprises a nonplasticizing 1,2-epoxide and an anhydride hardener. The patent states that the 1,2-epoxide includes glycidyl ethers of various polyhydric phenols, and dihydroxydinaphthylmethane is cited as one example of the polyhydric phenols. The patent, however, does not describe diglycidyl ethers of alpha, alpha'-dihydroxy-2,2'-(or 4,4'-)dinaphthylmethane.

The specification of Japanese Laid-Open Patent Publication No. 121,900/1974 discloses a method of producing a curable epoxy resin which comprises reacting an epoxy resin, an N,N'-bisimide and a polyamine under heat in the presence of an organic peroxide. The epoxy resin is a glycidyl ether of a mononuclear or polynuclear polyhydric phenol, and the specification exemplifies 1,5-dihydroxynaphthalene, 2,7-dihydroxynaphthalene, 2,6-dihydroxynaphthalene, bis-(4-hydroxynaphthyl)ether and bis-(4-hydroxy-3-chloronaphthyl)ether as the polynuclear polyhydric phenol. The Japanese patent document fails to describe any other polynuclear polyhydric phenols, and any specific examples of glycidyl ethers of polynuclear polyhydric phenols.

The specification of U.S. Pat. No. 4,368,298 discloses a method of producing a novolac-type epoxy resin, which comprises subjecting a halohydrin ether compound derived from a phenol compound to addition-polymerization with an aldehyde compound in the presence of an acid catalyst, and treating the resulting product with a cyclizing agent to form an epoxy ring. The phenol compounds disclosed in this specification are p-hydroxybenzoic acid, alphanaphthol, and compounds represented by the following formula

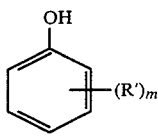

wherein R' represents a substituent group or atom, m represents an integer of from 0 to 4, and two or more R's may not necessarily be identical. The specification, however, fails to disclose specifically a halohydrin ether compound of alpha-naphthol. The present inventor repeated Example 1 of this Japanese patent document using alpha-naphthol instead of the phenol, and found that when a condensation product between a halohydrin compound of alpha-naphthol and an aldehyde compound was treated with an acid catalyst (sulfuric acid, gellation occurred, and the desired polyglycidyl ether could not be obtained.

It is an object of this invention to provide novel polyglycidyl ethers using alpha-naphthol as a phenol, and a process for production thereof.

Another object of this invention is to provide novel polyglycidyl ethers capable of giving cured products having excellent heat resistance and a low water absorption, and a process for production thereof.

Still another object of this invention is to provide novel cured products of the novel polyglycidyl ethers of the invention which have excellent heat resistance and a low water absorption.

Yet another object of this invention is to provide a novel composite material composed of a matrix of a cured product of a novel polyglycidyl ether according to the invention and a filler such as a fibrous reinforcing material dispersed therein.

A further object of this invention is to provide a novel cured product or composite material having excellent heat resistance of a level which has been unable to be achieved by conventional cured products of epoxy resins, namely having such an excellent heat resistance that even after it has been exposed to a high temperature of, for example, 200° C., it has a strength retention of, for example, 60%, preferably 70% or higher.

An additional object of this invention is to provide a novel cured product which has a high weight retention when exposed to very high temperatures of, for example, 500° C. or higher, namely a high char yield, and novel polyglycidyl ethers capable of giving such a cured product.

Other objects and advantages of this invention will become apparent from the following description.

According to this invention, these objects and advantages are achieved firstly by a polyglycidyl ether represented by the following formula (I)

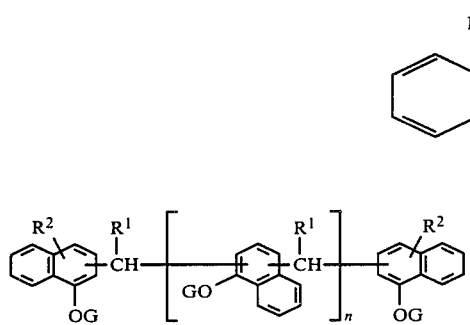
(I)

wherein
G represents a hydrogen atom,

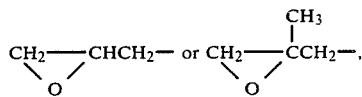

$R^1$ represents a hydrogen atom, an aliphatic hydrocarbon group having 1 to 10 carbon atoms, an alicyclic hydrocarbon group having 5 to 10 carbon atoms, an aromatic hydrocarbon group having 6 to 10 carbon atoms or a 5- or 6-membered heterocyclic group containing an oxygen or sulfur atom as a hetero atom, provided that the foregoing groups other than the hydrogen atom may be substituted by a halogen atom or the group —OG in which G is as defined, $R^2$ represents a hydrogen atom or the group $$-\underset{R^1}{\overset{}{\text{CHOG}}}$$

in which G and $R^1$ are as defined, and
n is 0 or a positive number,
provided that all groups G, all groups $R^1$ and all groups $R^2$ in the molecule may respectively be identical or different but at least two G groups in the molecule are

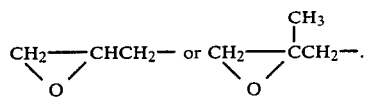

According to this invention, the polyglycidyl ether can be produced by condensing alpha-naphthol with at least one aldehyde represented by the following formula (II)

$$R_3—CHO \qquad (II)$$

wherein $R^3$ represents a hydrogen atom, an aliphatic hydrocarbon group having 1 to 10 carbon atoms, an alicyclic hydrocarbon group having 5 to 10 carbon atoms, an aromatic hydrocarbon group having 6 to 10 carbon atoms, or a 5- or 6-membered heterocyclic group containing an oxygen or sulfur atom as a hetero atom, provided that the foregoing groups other than the hydrogen atom may be substituted by a halogen atom or a hydroxyl group,
in the presence of an acid catalyst and optionally in the further presence of an inert reaction medium to form a polyol represented by the following formula (III)

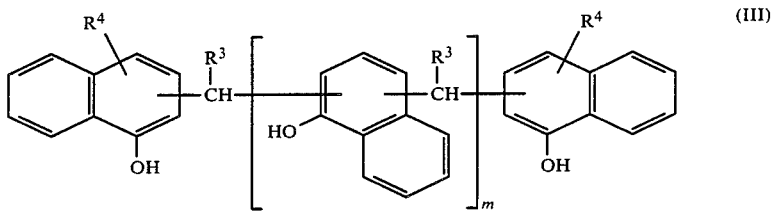
(III)

wherein $R^3$ is as defined, $R^4$ represents a hydrogen atom or $$-\underset{R^3}{\overset{}{\text{CHOH}}}$$

in which $R^3$ is as defined,
and m is 0 or a positive number, provided that all $R^3$ groups and all $R^4$ groups may respectively be identical or different,
and thereafter condensing the resulting polyol with an epihalohydrin represented by the following formula (IV)

(IV)

wherein $R^5$ represents a hydrogen atom or a methyl group, and X represents a halogen atom.

The starting materials used in this invention are alpha-naphthol and the aldehyde represented by formula (II).

In formula (II), $R^3$ represents a hydrogen atom, an aliphatic hydrocarbon group having 1 to 10 carbon atoms, an alicyclic hydrocarbon group having 5 to 10 carbon atoms, an aromatic hydrocarbon group having 6 to 10 carbon atoms, or a 5- or 6-membered heterocyclic group containing an oxygen or sulfur atom as a hetero atom. The foregoing groups other than the hydrogen atom may be substituted by a hydroxyl group or a halogen atom such as chlorine or bromine.

The aliphatic hydrocarbon group having 1 to 10 carbon atoms may be a linear or branched saturated or unsaturated hydrocarbon group, preferably a saturated hydrocarbon group having 1 to 10 carbon atoms. Examples of the aliphatic hydrocarbon group having 1 to 10 carbon atoms include unsubstituted alkyl groups having 1 to 10 carbon atoms such as methyl, ethyl, propyl, butyl, pentyl, hexyl, heptyl, octyl, nonyl and decyl; substituted alkyl groups having 1 to 10 carbon atoms such as chloromethyl, hydroxyethyl and chloroethyl; and substituted or unsubstituted alkenyl groups having 3 to 10 carbon atoms such as propen-1-yl, buten-1-yl and 3-fluoropropen-1-yl.

Examples of the alicyclic hydrocarbon group having 5 to 10 carbon atoms include cyclopentyl, cyclohexyl, chlorocyclohexyl, hydroxycyclohexyl, bromocyclohexyl and decalyl.

Examples of the aromatic hydrocarbon group having 6 to 10 carbon atoms include phenyl, hydroxyphenyl, fluorophenyl, bromophenyl, naphthyl and hydroxynaphthyl.

Examples of the 5- or 6-membered heterocyclic group containing an oxygen or sulfur atom are furyl, thienyl and pyranyl.

$R^2$ represents a hydrogen atom, a substituted or unsubstituted alkyl group having 1 to 10 carbon atoms, an alicyclic hydrocarbon group having 5 to 10 carbon atoms, or an aromatic hydrocarbon group having 6 to 10 carbon atoms. Above all, hydrogen, methyl, ethyl, propyl, butyl, cyclohexyl, phenyl, hydroxyphenyl, fluorophenyl and chlorophenyl are preferred, and hydrogen, phenyl, hydroxyphenyl, fluorophenyl and chlorophenyl are more preferably used. Hydrogen and hydroxyphenyl are especially preferred.

The aldehyde represented by formula (II) preferably includes formaldehyde, acetaldehyde, propionaldehyde, butyraldehyde, cyclohexyl aldehyde, benzaldehyde, p-hydroxybenzaldehyde and p-chlorobenzaldehyde.

According to the process of this invention, alpha-naphthol is condensed with the aldehyde of formula (II) in the presence of an acid catalyst to form the polyol of formula (III). One or more of the aldehydes of formula (II) may be used. The condensation reaction can be carried out in the absence of a reaction medium. Or it may be carried out in the presence of an inert reaction medium.

The proportion of the aldehyde used may be adjusted according to the desired degree of polymerization of the final resin. Usually, it is 0.5 to 1.5 moles per mole of alpha-naphthol.

Examples of the acid catalyst include protonic acids, for example mineral acids such as nitric acid, sulfuric acid, hydrochloric acid and phosphoric acid, organic sulfonic acids such as methanesulfonic acid and toluenesulfonic acid and organic carboxylic acids such as oxalic acid; and Lewis acids such as boron trifluoride, boron trifluoride etherate, aluminum chloride, tin chloride, zinc chloride, iron chloride and titanium chloride. Of these, the protonic acids are preferred, and hydrochloric acid, sulfuric acid, methanesulfonic acid and toluenesulfonic acid are especially preferred.

The amount of the catalyst used may be 0.001 to 0.05 mole per mole of the starting alpha-naphthol.

The condensation reaction between alpha-naphthol and the aldehyde is carried out usually at a temperature of 80° to 250° C.

Alternatively, the condensation reaction may be carried out at 80° to 150° C. in the early stage, and thereafter at a higher temperature. The reaction time may, for example, be 1 to 20 hours.

The condensation reaction may be carried out in an inert reaction medium, preferably in an aprotic inert reaction medium, for example, an aromatic hydrocarbon such as toluene, chlorobenzene, dichlorobenzene, nitrobenzene and diphenyl ether or an ether such as a dimethyl ether of ethylene glycol or diethylene glycol.

When the condensation reaction is carried out without a reaction medium, the melting point of the polyol (III) increases as its degree of polymerization increases and therefore it is desirable to increase the reaction temperature accordingly.

Thus, the above condensation reaction gives the polyol of formula (III).

In formula (III), $R^3$ is as defined for formula (II), and $R^4$ represents a hydrogen atom or

and m is 0 or a positive number.

It will be understood that in formula (III),

as a group bridging the alpha-naphthol skeletons, and

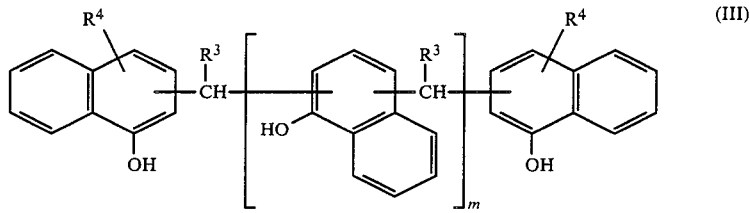

as a substituent on the alpha-naphthol skeleton are derived from the aldehyde of formula (II).

The alpha-naphthol skeleton in the parenthesis have two bridging groups

which are located mainly at the ortho- and para-positions to the hydroxyl group of the alpha-naphthol skeleton. The alpha-naphthol skeleton at each terminal of the molecule has the bridging group

mainly at the ortho- or para-position to the hydroxyl group of the alpha-naphthol skeleton. When the alpha-naphthol has a substituent

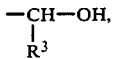

it is located at the ortho-position when the bridging group is at the para-position or at the para-position when the bridging group is at the ortho-position.

m is 0 or a positive number, preferably a positive number of not more than 10, especially preferably 1 to 10.

For example, when $R^3$ has a hydroxyl group, m is not more than 5, preferably 1 to 3. When $R^3$ has no hydroxyl group, m is 1 to 10, preferably 2 to 7.

The polyol in accordance with this invention preferably has a hydroxyl value of 120 to 320 g/mole, more preferably 120 to 270 g/mole, especially preferably 120 to 180 g/mole.

According to the process of this invention, the polyol is then condensed with the epihalohydrin of formula (IV).

In formula (IV), $R^5$ represents a hydrogen atom or a methyl group, and X represents a halogen atom such as a chlorine or bromine atom. Examples of preferred epihalohydrins of formula (IV) are epichlorohydrin, epibromohydrin, beta-methylepichlorohydrin and beta-methylepibromohydrin. Epichlorohydrin is especially preferred.

Advantageously, this condensation reaction is carried out by (1) reacting the polyol of formula (III) with the epihalohydrin of formula (IV) in the presence of an alkali metal hydroxide or an alkaline earth metal hydroxide, or (2) subjecting the polyol of formula (III) and the epihalohydrin of formula ((IV) to ring-opening addition reaction in the presence of a quaternary ammonium salt to form the corresponding polyhalohydrin ether, and thereafter cyclocondensing the resulting polyhalohydrin ether in the presence of an alkali metal hydroxide or an alkaline earth metal hydroxide.

In the presence (1) above, sodium hydroxide and potassium hydroxide are preferred examples of the alkali metal hydroxide, and calcium hydroxide, for example, is preferred as the alkaline earth metal hydroxide. The alkali metal hydroxide or the alkaline earth metal hydroxide is added to the reaction system preferably in the form of a solid or a concentrated aqueous solution (for example in a concentration of 10 to 50% by weight). The reaction is carried out preferably at a temperature between 60° and 120° C. The epihalohydrin of formula (IV) is used in an amount of preferably 5 to 20 moles, more preferably 10 to 15 moles, per hydroxyl equivalent of the polyol of formula (III). The alkali metal hydroxide or the alkaline earth metal hydroxide is used in a proportion of preferably 0.8 to 1.2 moles per hydroxyl equivalent of the polyol of formula (III).

In the reaction (2), the quaternary ammonium salt is preferably a compound represented by the following formula (V)

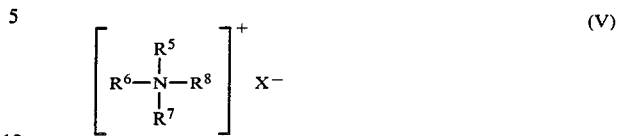

wherein $R^5$, $R^6$, $R^7$ and $R^8$ may be identical or different and each represents an alkyl group having 1 to 6 carbon atoms or a benzyl group, and X X represents a halogen atom.

In formula (V), the alkyl group having 1 to 6 carbon atoms may be linear or branched, and includes, for example, methyl, ethyl, propyl, butyl, pentyl and hexyl. The halogen atom is, for example, chlorine, bromine or iodine. Examples of preferred quaternary ammonium salts of formula (V) are tetramethyl ammonium chloride, tetraethyl ammonium bromide and trimethylbenzyl ammonium chloride.

The epihalohydrin of formula (IV) is used in a proportion of preferably 5 to 20 moles, more preferably 5 to 15 moles, per hydroxyl equivalent of the polyol of formula (III). The quaternary ammonium salt is used in a catalytic amount. For example, its amount is 0.001 to 0.02 mole per hydroxyl equivalent of the polyol of formula (III). The reaction can be carried out at a temperature of, for example, 70° to 150° C.

As a result, the ring-opening addition reaction between the epihalohydrin (IV) and the polyol (III) gives the corresponding polyhalohydrin ether in which at least a part of the hydroxyl group of the polyol has been converted to a halohydrin ether group represented by the following formula (IV)

wherein $R^5$ is as defined hereinabove.

The resulting polyhalohydrin ether is thereafter cyclocondensed in the presence of an alkali metal hydroxide or an alkaline earth metal hydroxide. The same alkali metal hydroxides or alkaline earth metal hydroxides as described above can be used in the same amounts.

This cyclocondensation can be carried out at a temperature of, for example, 60° to 120° C.

The reaction (2) including the ring-opening addition reaction and the cyclocondensation usually ends in 1 to 10 hours.

The reaction mixture obtained by the process of this invention is usually distilled to remove the unreacted epihalohydrin (IV), and subsequently extracted with water or filtered to remove inorganic or organic impurities, for example water-soluble inorganic impurities. Thus, the polyglycidyl ether of the invention represented by formula (I) is obtained.

The polyglycidyl ether so obtained may be further purified by heat-treating it with an alkaline aqueous solution of an alkali metal hydroxide such as sodium hydroxide or potassium hydroxide at 60° to 100° C. for 1 to 20 hours to reduce its halogen content. In the separation and purification of the polyglycidyl ether in the process of this invention and in the aforesaid treatment with the alkaline aqueous solution, the polyglycidyl ether is preferably dissolved in an organic solvent such as methyl butyl ketone, benzene, toluene, xylene, ethylbenzene or cumene.

The novel polyglycidyl ether provided by this invention is represented by the following formula (I).

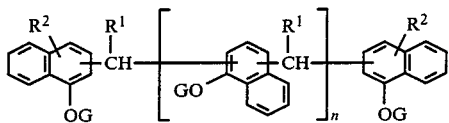
(I)

In formula (I), G represents a hydrogen atom,

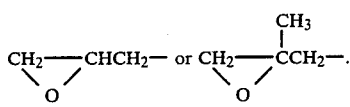

All G groups in the molecule may be identical or different, but at least two G groups in the molecule are

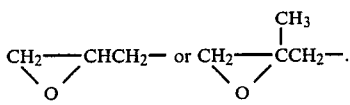

G is preferably

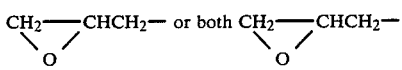

and hydrogen atom.

$R^1$, correspondingly to the definition of $R^3$ in formula (III), represents a hydrogen atom, an aliphatic hydrocarbon group having 1 to 10 carbon atoms, an alicyclic hydrocarbon group having 5 to 10 carbon atoms, an aromatic hydrocarbon group having 6 to 10 carbon atoms or a 5- or 6-membered heterocyclic group containing an oxygen or sulfur atom as a hetero atom. Specific examples of these groups and their preferred species are the same as those described hereinabove for $R^3$.

When $R^1$ is not a hydrogen atom but the other groups described above, these groups may be substituted by a halogen atom or a group of the formula —OG. The halogen atom is, for example, a chlorine or bromine atom, and the group —OG is —OH,

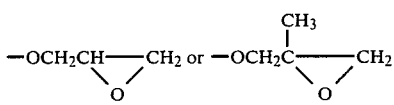

according to the definition of G.

$R^2$ represents a hydrogen atom or the group

and all $R^1$ groups in the molecule may be identical or different.

The relation of the bridging group

and the substituent

to the group —OG is the same as that of the bridging group

and the substituent

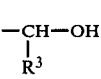

in formula (III) to the hydroxyl group on the ring.

n is 0 or a positive number, preferably a positive number, for example a positive number of not more than 10, prefeably 1 to 10. For example, when $R^1$ includes the group —OG in which G is

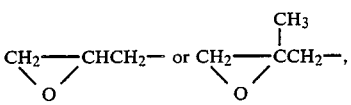

n is a number of not more than 5, preferably 1 to 3. When $R^1$ does not have the group —OG in which G is as defined above, n is 1 to 10, preferably 2 to 7.

When n is 0 in general formula (I) representing the polyglycidyl ether of this invention, the general formula (I) can be written as follows:

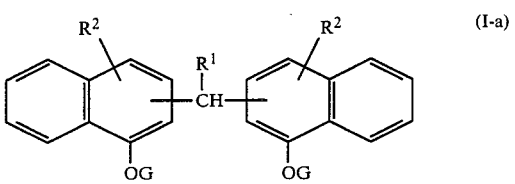
(I-a)

When in formula (I)-a, $R^1$ is a hydrogen atom, one $R_2$ is a hydrogen atom, the other $R^2$ is $CH_2OG$, and G is

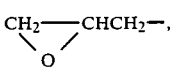

the compound of formula (I)-a can be represented by the following formula.

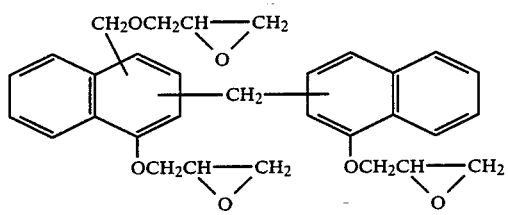

Other specific examples of the polyglycidyl ether of this invention will be understood from the above example.

The polyglycidyl ether of this invention preferably has at least 3, more preferably 3 to 10, especially preferably 4 to 7, groups of the formula

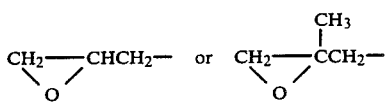

in the molecule. Such a polyglycidyl ether is obtained when $R^2$ is a hydrogen and n is at least 1, and when $R^2$ is

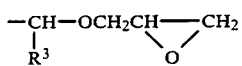

and n is 0.

Preferably, the polyglycidyl ether of this invention has an epoxy equivalent of about 180 to about 500 g/equivalents, more preferably about 180 to about 450 g/equivalents, especially preferably about 180 to about 280 g/equivalents, and a melting point of about 50° to about 150° C.

The novel polyglycidyl ethers of this invention can be cured with conventional curing agents (see, for example, "Epoxy Resins", edited by Hiroshi Kakiuchi and published by Shokodo on Sept. 30, 1970, pages 109-149). Suitable curing agents include, for example, amines, acid anhydrides, polyamide resins, polysulfide resins, boron trifluoride-type amine complexes, novolak resins and dicyandiamide.

Specific examples are primary or secondary aliphatic amines such as diethylene triamine, triethylene tetramine, 1,3-diaminocyclohexane, isophorone diamine and m-xylylenediamine; aromatic amines such as meta-phenylenediamine, para-phenylenediamine, 4,4'-diaminodiphenylmethane, 4,4'-diaminodiphenylsulfone, 3,3'-diaminodiphenylsulfone, 2,4-tolylenediamine, 4,4'-diaminodiphenylether, 3,4'-diaminodiphenylether and aniline-formaldehyde resin; adducts of the aforesaid aliphatic amines or aromatic amines with monoepoxy compounds (ethylene oxide, phenyl glycidyl ether and butyl glycidyl ether), or polyepoxy compounds (a diglycidyl ether of bisphenol A and a diglycidyl ether of resorcinol); acid anhydrides such as phthalic anhydride, hexahydrophthalic anhydride, Nadic anhydride, methylNadic anhydride, pyromellitic anhydride, benzophenotenetracarb oxylic anhydride, trimellitic anhydride, glycerin tristrimellitate and ethylene glycol bistrimellitate; polyamide resins derived from dimeric acid and diethylene tetramine or triethylene tetramine; polysulfide resins having mercapto groups at both ends; complexes of boron trifluoride and amines such as aniline, N-methylaniline, benzylamine and ethylamine; low-molecular-weight novolak resins obtained from phenol or cresol and formalin; and dicyandiamide.

When the novel polyglycidyl ethers of this invention are cured with aromatic polyamines, dicyandiamide, or complexes of boron trifluoride and amines, they exhibit particularly good effects.

Aromatic diamines such as 3,3'- or 4,4'-diaminodiphenylsulfone and dicyandiamide are preferred, and 3,3'- or 4,4'-diaminodiphenylsulfone is especially preferred.

The amounts of the amines, polyamide resins, polysulfide resins, boron trifluoride/amine complexes and novolak resins used as the curing agents are such that the amount of active hydrogens in these curing agents is 0.5 to 1.5 moles, preferably 0.8 to 1.2 moles, per epoxy group equivalent of the polyglycidyl ether. The amount of the acid anhydride as the curing agent is 0.5 to 1.0 mole, preferably 0.5 to 0.9 mole, per epoxy group equivalent in the polyglycidyl ether. The amount of dicyandiamide as the curing agent is 1/20 to ⅓ mole, preferably 1/10 to ¼ mole, per epoxy equivalent in the polyglycidyl ether.

As required, a minor proportion of a curing promoter may be used in the curing reaction.

Examples of the curing promoter are tertiary amines such as triethylamine, tributylamine and dimethylbenzylamine; phenols such as phenol, cresol, butylphenol, nonylphenol, chlorophenol, resorcinol and polyvinylphenol; imidazoles such as imidazole and 2-ethyl-4-methylimidazole; and salts thereof such as acetates thereof.

The polyglycidyl ether of this invention can be cured in the presence of a curing agent and optionally a curing promoter. Since the polyglycidyl ether of this invention has excellent solubility in solvents, it can be cured by dissolving it in an aprotic organic solvent, and uniformly dispersing or dissolving a curing agent and optionally a curing promoter in the solution, and thereafter removing the solvent.

Illustrative of the aprotic organic solvent used for this purpose are ketones such as acetone, methyl ethyl ketone, methyl butyl ketone and diethyl ketone; alcohols such as methyl Cellosolve and ethyl Cellosolve; cyclic ethers such as dioxane and tetrahydrofuran; amides such as dimethylformamide, dimethylacetamide and N-methylpyrrolidone; and aromatic hydrocarbons such as benzene, toluene, xylene and cumene.

The curing reaction of the polyglycidyl ether of this invention is carried out preferably at a temperature of at least 60° C., more preferably at a temperature between 100° and 250° C.

The curing time is usually 0.5 to 5 hours. The heat resistance of the resulting cured product can be further improved by curing it preferably at a temperature of at least 150° C.

The polyglycidyl ether of this invention has a low melting point and excellent solubility. For example, the polyglycidyl ethers of the invention cured with the aforesaid aromatic polyamines, dicyandiamide, complexes of boron trifluoride and amines, or acid anhydride have a glass transition temperature of at least 230° C., preferably at least 250° C., especially preferably at least 280° C., and a water absorption in water at 100° C. of less than 4.0%, and show excellent water resistance. In view of the fact that cured products of polyglycidyl ethers obtained by using phenol instead of alpha-naphthol have a water absorption of at least 4%, it is evident that the cured resins obtained from the polyglycidyl ethers of this invention have excellent heat resistance and water resistance.

It can be ascertained by gas chromatography and mass spectrometry that when a cured resin obtained from the polyglycidyl ether of this invention is heat-decomposed at 480° C. for 2 minutes, the decomposition product contains alpha-naphthol.

Since the cured resin obtained from the polyglycidyl ether of this invention has such a characteristic feature, a composite material having excellent heat resistance can be produced by mixing the polyglycidyl ether of the invention with a filler and then curing the polymer.

Various fillers can be used to produce the composite material of this invention. Typically, talc, silica, clay, mica, asbestos and inorganic or organic fibers well known as reinforcing materials for composite materials can be used. Preferred examples of the inorganic fibers are carbon fibers, glass fibers, boron fibers, silicon carbide fibers, alumina fibers and silica alumina fibers. Examples of the organic fibers are aramide fibers and polyester fibers. So-called advanced fibers such as carbon fibers and aramide fibers are especially preferably used. PAN-type carbon fibers derived from polyacrylonitrile fibers as a main starting material, and pitch-type carbon fibers derived from pitch from coal or petroleum as a material are used as the carbon fibers. The fibers may be in the form of long fibers or short fibers or in a molded form such as a woven fabric.

Preferably, the composite material in accordance with this invention is composed of (A) a matrix resin and (B) reinforcing fibers, but may also contain another filler, a pigment, a curing promoter, a stabilizer, etc.

The ratio of the matrix resin (A) composed of the novel polyglycidyl ether of the invention and a curing agent for an epoxy resin to the fibrous reinforcing material (B) in the composite material of this invention may be selected to suit the purpose of using the composite material. Usually, the weight ratio of (A) to (B) is from 10:90 to 80:20, preferably from 30:70 to 70:30.

In forming the composite material of this invention, the matrix resin and the filler may be combined by any desired method such as mixing, kneading or lamination. For example, reinforcing fibers aligned in one direction may be impregnated with the matrix resin or its solution. Or the fibers may first be molded into the form of a woven fabric such as plain weave or satin weave fabric, and then impregnated with the matrix resin.

Useful molded articles can be produced from the composite material of this invention by various molding methods. Compression molding is a typical molding method whereby the composite material may be compressed mechanically in a mold of a predetermined shape, or compressed in an autoclave by the pressure of a gas. Other conventional molding methods such as lamination and transfer molding may also be used.

The following examples illustrate the present invention more specifically. All parts in these examples are by weight.

EXAMPLE 1

Oxalic acid (1.6 parts), 16 parts of water and 144 parts of chlorobenzene were added to 144 parts of alpha-naphthol, and the mixture was heated to 100° C. to form a solution. Then, 68.6 parts of 35% formalin was added, and the mixture was reacted at 100° to 120° C. for 8 hours. One hundred parts of chlorobenzene was removed by distillation together with water. The remainder was transferred to a vat, and dried at 120° C. to obtain 153 parts of alpha-naphthol novolak (polyol) having a melting point of 170° C. and a molecular weight (determined by a cryoscopic method in dioxane) of 630.

Then, 920 parts of epichlorohydrin was added to the alpha-naphthol novolak, and 79 parts of a 50% aqueous solution of sodium hydroxide was added at 100° C. over 2.5 hours. After the addition, the reaction was further carried out under heat for 30 minutes. During this time, water was removed under reduced pressure as an azeotrope with epichlorohydrin. After the reaction, epichlorohydrin was removed under reduced pressure, and toluene was added to dissolve the reaction mixture. The solution was filtered to remove the unreacted sodium hydroxide and the gel and sodium chloride formed by the reaction.

The solution was heated under reduced pressure to remove the solvent, and dissolved in 170 parts of methyl isobutyl ketone. The solution was reacted at 90° C. for 8 hours together with 79 parts of a 10% aqueous solution of sodium hydroxide.

A mixture of methyl isobutyl ketone and epichlorohydrin was added to the reaction mixture to dilute it, followed by washing with water, then with an aqueous solution of phosphoric acid and again with water. The solvent was removed under reduced pressure to give 160 parts of polyglycidyl ether having an epoxy equivalent of 240 (g/eq), a molecular weight (determined by a cryoscopic method in dioxane) of 1070 and a melting point of 120° C.

EXAMPLES 2 TO 4

In each run, alpha-naphthol novolak having the properties shown in Table 1 was synthesized under the conditions shown in Table 1 in the same way as in Example 1 except that the amount of 35% formalin was changed to 59.9 parts, 77.0 parts and 43.0 parts, respectively. Subsequently, using the alpha-naphthol novolak, a polyglycidyl ether was synthesized under the conditions shown in Table 2. The results are shown in Table 3. Tables 1, 2 and 3 also give the data of Example 1.

TABLE 1

| Example | Alpha-naphthol (parts) | Formalin (parts) | 10% aqueous oxalic acid solution (parts) | Chlorobenzene (parts) | Reaction temperature (°C.) | Reaction time (hr) | Amount yielded (parts) | Molecular weight | Melting point (°C.) | Degree of polymerization |
|---|---|---|---|---|---|---|---|---|---|---|
| 1 | 144 | 68.6 | 16 | 144 | 100–120 | 8.0 | 153 | 630 | 170 | 4.1 |
| 2 | 144 | 59.9 | 16 | 144 | 100–120 | 8.0 | 150 | 540 | 155 | 3.5 |
| 3 | 144 | 77.0 | 16 | 144 | 100–120 | 8.0 | 154 | 900 | 180 | 5.8 |
| 4 | 144 | 43.0 | 16 | 144 | 100–120 | 8.0 | 148 | 310 | 95 | 2.0 |

TABLE 2

| | 1st step | | | | | 2nd step | | | |
|---|---|---|---|---|---|---|---|---|---|
| Example | Alpha-naphthol novolak (parts) | Epi-chlorohydrin (parts) | 50% NaOH (parts) | Reaction temperature (°C.) | Reaction time (hr) | MIBK (parts) | 10% NaOH (parts) | Reaction temperature (°C.) | reaction time (hr) |
| 1 | 153 | 920 | 79 | 100 | 3.0 | 170 | 79 | 90 | 8.0 |
| 2 | 150 | 1250 | 77 | 100 | 2.5 | 180 | 77 | 90 | 8.0 |
| 3 | 154 | 1100 | 74 | 100 | 3.5 | 190 | 74 | 90 | 8.0 |
| 4 | 145 | 1000 | 75 | 100 | 2.5 | 170 | 75 | 90 | 8.0 |

TABLE 3

| Example | Amount yielded (parts) | Epoxy-equivalent | Molecular weight | Melting point (°C.) | Elemental analysis C (%) | Elemental analysis H (%) |
|---|---|---|---|---|---|---|
| 1 | 160 | 240 | 1070 | 120 | 78.4 | 5.7 |
| 2 | 163 | 220 | 740 | 105 | 77.8 | 5.7 |
| 3 | 155 | 245 | 1500 | 125 | 79.0 | 5.8 |
| 4 | 180 | 220 | 440 | —(*) | 76.8 | 6.0 |

(*)The product was a transparent substance which was hardly flowable at room temperature but was readily deformed when pressed.

EXAMPLE 5

144 Parts of alpha-naphthol and 82 parts of p-hydroxybenzaldehyde were heat-melted at 130° C., and 0.2 part of 36% hydrochloric acid and 0.3 part of p-toluenesulfonic acid were added. The mixture was reacted at 100° C. for 1 hour and subsequently at 190° to 200° C. for 8 hours. Water formed as a result of the reaction was distilled out of the reaction system. The resulting reaction mixture was taken out of the reactor, pulverized, washed with hot water and dried. There was obtained 207 parts of alpha-naphthol novolak having a melting point of more than 300° C. and a molecular weight, determined by a cryoscopic method in dioxane, of 535 (containing 2.6 alpha-naphthol moieties on an average, 1.6 p-hydroxybenzaldehyde moieties on an average, and 4.2 hydroxyl groups per molecule). To 200 parts of alpha-naphthol novolak were added 1440 parts of epichlorohydrin and 2.4 parts of trimethylbenzyl ammonium chloride, and the mixture was heated at 110° to 120° C. for 3 hours. Then, while the mixture was heated at 80° C. under reduced pressure, 135 parts of a 50% aqueous solution of sodium hydroxide was added over 2 hours. During this time, water was removed out of the reaction system as an azeotrope with epichlorohydrin. Then, an aqueous solution of sodium hydroxide was added, and the reaction was further carried out at the same temperature for 2 hours while removing water out of the reaction system. After the reaction, epichlorohydrin was evaporated under reduced pressure, and the residue was extracted with methyl isobutyl ketone and washed with water to remove sodium hydroxide and sodium chloride, followed by washing with an aqueous solution of phosphoric acid. The methyl isobutyl ketone solution was further washed with water until it became neutral. Finally, methyl isobutyl ketone was removed under reduced pressure to obtain 250 parts of the desired polyglycidyl ether.

The polyglycidyl ether had a melting point of 110° C., an epoxy equivalent, determined by a hydrochloric acid dioxane method, of 240 (g/eq), and a molecular weight, determined by a cryoscopic method in dioxane, of 800. The elemental analysis of the polyglycidyl ether showed 77.8% C and 5.5% H.

EXAMPLES 6 TO 11

In each run, alpha-naphthol novolak described in Table 4 was produced in accordance with the procedure of Example 5 under the conditions shown in Table 4. The novolak was then reacted with an epihalohydrin under the conditions shown in Table 5 to obtain the polyglycidyl ether shown in Table 5.

TABLE 4

| | Starting materials | | | | | Reaction conditions | | | Analytical values | |
|---|---|---|---|---|---|---|---|---|---|---|
| Example | Amount of alpha-naphthol (parts) | Aldehyde Kind | Aldehyde Amount (parts) | Catalyst Kind | Catalyst Amount (parts) | Temperature (°C.) | Time (hr) | Amount yielded (parts) | Molecular weight | Melting point (°C.) |
| 6 | 144 | Acetaldehyde | 44 | 35% HCl | 0.3 | 100 / 140 | 12 / 6 | 156 | 650 | 120 |
| 7 | " | Butyraldehyde | 65 | " | 0.5 | 100 / 140 | 5 / 7 | 191 | 640 | 145 |
| 8 | " | Cyclohexylcarbaldehyde | 95.2 | " | 0.3 | 100 / 140 | 2.5 / 5 | 213 | 720 | 120 |
| 9 | " | Benzaldehyde | 84.8 | 35% HCl / PTS (*) | 0.4 / 0.3 | 100 / 170 | 1 / 9 | 210 | 705 | 240 |
| 10 | " | p-Chlorobenzaldehyde | 119.5 | 35% HCl / PTS (*) | 0.5 / 0.4 | 100 / 180 | 1 / 8 | 246 | 940 | 235 |
| 11 | " | Formaldehyde | 77.2 | 10% Oxalic acid | 16 | 100 / 120 | 3 / 5 | 152 | 735 | 170 |

(*) PTS: p-Toluenesulfonic acid

TABLE 5

| Example | 1st step (*1) Amount of alpha-naphthol novolak (parts) | Epihalohydrin Kind | Epihalohydrin Amounts (parts) | Amount of ammonium salt (parts) | 2nd step (*2) Amount of 50% NaOH (parts) | Reaction conditions Temperature (°C.) | Reaction conditions Time (hr) | Amount yielded (parts) | Analytical value Epoxy equivalent (g/eq) | Molecular weight | Melting point (°C.) | Elemental analysis C % | Elemental analysis H % |
|---|---|---|---|---|---|---|---|---|---|---|---|---|---|
| 6 | 155 | Epichlorohydrin | 1100 | 2.0 | 87 | 100 | 4.0 | 168 | 240 | 890 | 110 | 79.8 | 6.2 |
| 7 | 190 | Epichlorohydrin | 1500 | 2.0 | 88 | " | 2.5 | 210 | 310 | 940 | 110 | 78.8 | 6.9 |
| 8 | 210 | Epichlorohydrin | 1500 | 1.9 | 88 | " | 3.0 | 240 | 360 | 970 | 80 | 80.8 | 7.3 |
| 9 | 200 | Epichlorohydrin | 1650 | 2.0 | 84 | " | 2.5 | 220 | 375 | 900 | 150 | 83.2 | 5.8 |
| 10 | 240 | Epichlorohydrin | 1500 | 2.0 | 86 | " | 4.0 | 270 | 400 | 1300 | 160 | 73.4 | 4.8 |
| 11 | 150 | β-Methylepichlorohydrin | 1600 | 2.0 | 88 | 80 | 4.0 | 175 | 270 | 1200 | 150 | 78.3 | 6.2 |

(*1) Ring-opening addition reaction (110–120° C., 3 hrs.)
(*2) Cyclizing reaction The characteristic absorptions of the infrared absorption spectra of the polyglycidyl ethers synthesized in Examples 1 to 11 are shown in Table 6 below.

raised at an elevating rate of 10° C./in. by means of DMA (Dynamic Mechanical Analyzer, Model 1090 of E. I. du Pont de Nemours & Co.), and the glass transi-

TABLE 6

| Polyglycidyl ether (Example No.) | Components of polyglycidyl ether Aldehyde component | Components of polyglycidyl ether Phenol component | Components of polyglycidyl ether Glycidyl component | Characteristic absorptions of infrared spectrum (cm$^{-1}$) Epoxy group | Characteristic absorptions of infrared spectrum (cm$^{-1}$) Aromatic ring | Characteristic absorptions of infrared spectrum (cm$^{-1}$) Ether |
|---|---|---|---|---|---|---|
| 1,2,3,4 | Formaldehyde | Alpha-naphthol | Epichlorohydrin | 910, 860, 840 | 810, 760 | 1000 |
| 5 | p-Hydroxybenzaldehyde | Alpha-naphthol | Epichlorohydrin | 905, 855, 835 | 805, 790, 765 | 1020, 990 |
| 6 | Acetaldehyde | Alpha-naphthol | Epichlorohydrin | 905, 850 | 810, 760 | 995 |
| 7 | Butyraldehyde | Alpha-naphthol | Epichlorohydrin | 905, 850, 830 | 810, 760 | 1000 |
| 8 | Cyclohexylcarbaldehyde | Alpha-naphthol | Epichlorohydrin | 905, 850, 830 | 795, 760 | 990 |
| 9 | Benzaldehyde | Alpha-naphthol | Epichlorohydrin | 905, 850, 830 | 805, 760, 690 | 995 |
| 10 | p-Chlorobenzaldehyde | Alpha-naphthol | Epichlorohydrin | 903, 850, 830 | 803, 760, | 990 |
| 11 | Formaldehyde | Alpha-naphthol | β-methylepichlorohydrin | 895 | 805, 760 | 995 |

EXAMPLES 12 TO 26 AND COMPARATIVE EXAMPLES 1 AND 2

Cured molded products having the properties shown in Table 7 were produced under the conditions shown in Table 7-1 from the polyglycidyl ethers obtained in Examples 1 to 11. Thus, in each run, a curing agent was added to 100 parts of the polyglycidyl ether, and the mixture was uniformly dissolved in 150 parts of acetone or methyl Cellosolve. The solvent was evaporated from the solution at 60° C. under reduced pressure, and the residue was cured in a customary manner by using a press-forming device under 10 kg/cm² under the temperature time conditions indicated in Table 7-1 to form molded pieces having a thickness of 3 mm, a width of 6 mm and a length of 120 mm. The molded pieces were post-cured at 220° C. for 4 hours. The temperature was tion temperatures of the molded pieces were measured. The results are also shown in Table 7-1. After the post-curing, the molded pieces were boiled for 10 days in water at 100° C., and their water absorptions were measured from an increase in weight. The results are also shown in Table 7-1.

For comparison, test pieces were prepared from N,N,N',N'-tetraglycidyl-4,4'-diaminodiphenylmethane (Comparative Example 1) and a diglycidyl ether of bisphenol A (Comparative Example 2), and their properties were examined. The results obtained are also shown in Table 7-1.

The cured products of Example 14 and Comparative Example 1 were each subjected to TGA analysis (temperature elevation rate 20° C./min.; atmosphere air, 12 ml/min.). The results are shown in Table 7-2.

TABLE 7-1

| Example | Polyglycidyl ether (*1) Aldehyde component of novolak | DP of novolak | Curing agent (*2) Kind | Amount (phr) | Curing conditions Temperature (°C.) | Time (hr) | Tg (°C.) | Water content (%) |
|---|---|---|---|---|---|---|---|---|
| 12 | Formaldehyde | 2 | DDS | 25 | 200 | 0.5 | 235 | 2.7 |
| 13 | " | 3.5 | DDS | 25 | 180 | 0.5 | 290 | 2.6 |
| 14 | " | 4.1 | DDS | 25 | 180 | 0.5 | 310 | 2.5 |
| 15 | Acetaldehyde | 3.2 | DDS | 25 | 180 | 0.5 | 260 | 2.5 |
| 16 | Benzaldehyde | 3.4 | DDS | 17 | 200 | 1.0 | 285 | 2.3 |
| 17 | p-Hydroxybenzaldehyde | 4.6 | DDS | 25 | 180 | 0.5 | 300 | 2.8 |
| 18 | Butyraldehyde | 3.5 | DDS | 20 | 200 | 1.0 | 265 | 2.5 |
| 19 | (cyclohexyl)-CHO | 3.4 | DDS | 17 | 200 | 1.0 | 260 | 2.6 |
| 20 | Cl-(phenyl)-CHO | 4.0 | DDS | 15 | 200 | 1.0 | 280 | 2.4 |
| 21 | Formaldehyde | 4.1 | 3,3'-DDS | 25 | 180 | 0.5 | 290 | 2.5 |
| 22 | " | 4.1 | MDA | 180 | 200 | 1.0 | 280 | 3.1 |
| 23 | " | 4.1 | Dicyandiamide | 8.2 | 190 | 1.0 | 270 | 3.4 |
| 24 | " | 4.1 | BF$_3$ ethylamine | 3 | 165 | 0.5 | 260 | 3.5 |
| 25 | " | 4.1 | 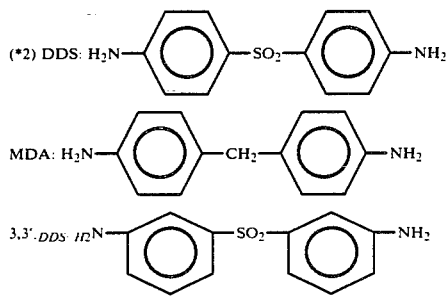 | 53 | 200 | 1.0 | 240 | 3.4 |
| 26 | " | 4.8 | DDS | 23 | 220 | 1.0 | 265 | 2.6 |
| Comp. Ex.1 | N,N,N',N'Ab,4 tetraglycidyl-4,4'-diaminodiphenylmethane | — | DDS | 59 | 180 | 1.0 | 245 | 6.7 |
| Comp. Ex. 2 | bisphenol A diglycidyl ether | — | DDS | 35 | 180 | 1.0 | 210 | 4.0 |

Note to Table 7-1:
(*1) In Example 26, a polyglycidyl ether obtained by using beta-methylepichloropydrin was used. In other Examples shown in Table 7-1 polyglycidyl ethers produced by using epichlorohydrin were used. The degree of polymerization of the novolak shows the number of hydroxyl groups in the molecule.

(*2) DDS: H$_2$N—(phenyl)—SO$_2$—(phenyl)—NH$_2$

MDA: H$_2$N—(phenyl)—CH$_2$—(phenyl)—NH$_2$ 3,3'-DDS: H$_2$N—(phenyl)—SO$_2$—(phenyl)—NH$_2$

TABLE 7-2

| | Cured products | |
|---|---|---|
| | Example 14 | Comparative Example 1 |
| Temperature (°C.) at which a weight retention of 60% by weight was obtained | 540 | 450 |
| Temperature (°C.) at which a weight retention of 50% by weight was obtained | 600 | 500 |

EXAMPLES 27 AND 28 AND COMPARATIVE EXAMPLE 3

To 25 parts of the polyglycidyl ether obtained in Example 1, 5.6 parts of 4,4'-diaminodiphenylsulfone and 30 parts of acetone were added to form a solution. Long carbon fibers (Toreka T 400, a product of Toray Inc.; 6000 filaments/3600 denier) were immersed in the resulting resin solution, and wound up on a drum while the resin solution was impregnated in the carbon fibers. Then, acetone was removed, and the residue was heat-treated to form prepregs.

The prepregs so obtained were stacked in a mold of a hot press device kept at 180° C., and cured under pressure. Then, they were maintained for 4 hours in a hot air circulating constant temperature vessel kept at 220° C. to perform post-curing to form a unidirectionally fiber-reinforced molded article having a thickness of 2 mm and a fiber content of 65% by volume.

For comparison, a composite material (reinforcing fibers: Toreka T 400, 65% by weight) was prepared in the same way as in Example 27 using N,N,N',N'-tetraglycidyl-4,4'-diaminodiphenylmethane as an epoxy resin (Comparative Example 3).

A test piece having a thickness of 1 mm and a width of 12.5 mm in a parallel part was cut out from the molded article, and subjected to a tensile test by an ordinary method. Furthermore, a test piece having a thickness of 2 mm and a width of 12.5 mm was prepared and subjected to a bending test.

Table 8 summarizes the dynamic properties of the resulting composite materials. It is seen from Table 8 that the molded articles in accordance with this invention maintain a very high retention of tensile strength and flexural strength at 200° C. This demonstrates the superiority of the composite material of this invention.

TABLE 8

| Test item | Measuring temperature | Example 27 | Comparative Example 3 |
|---|---|---|---|
| Tensile strength (kg f/mm$^2$) | Room temperature | 215 | 228 |
| | 200° C. | 212 (0.99) | 198 (0.87) |
| | −60° C. | 210 (0.98) | 219 (0.96) |
| Tensile modulus (10$^3$ kg f/mm$^2$) | Room temperature | 15.7 | 15.4 |
| Elongation (%) | Room temperature | 1.47 | 1.38 |
| Flexural strength (kg f/mm$^2$) | Room temperature | 224 | 239 |
| | 200° C. | 140 (0.63) | 130 (0.54) |
| Flexural modulus (kg f/mm$^2$) | Room temperature | 13.5 | 13.2 |
| | 200° C. | 13.5 (1.00) | 12.3 (0.93) |

The parenthesized figures are the ratios to the values measured at room temperature.

A test piece for measurement of flexural property was cut out from the composite material obtained in Example 27 in the same way as in Example 27, and maintained in a constant temperature vessel kept at a given temperature. It was subjected to a three-point bending test in the atmosphere of the vessel. The results are shown in Table 9. Table 9 demonstrates that while the conventional epoxy resin (Comparative Example 3) shows an abrupt reduction in property at a temperature of about 200° C., the composite material of this invention shows an excellent retention of property even at a high temperature above 200° C.

TABLE 9

| Measuring temperature | Example 27 | | Comparative Example 3 | |
|---|---|---|---|---|
| | Flexural strength (kg f/mm$^2$) | Flexural modulus (10$^3$ kg f/mm$^2$) | Flexural strength (kg f/mm$^2$) | Flexural modulus (10$^3$ kg f/mm$^2$) |
| Room temperature | 219 | 14.4 | 239 | 12.8 |
| 100° C. | 201 (0.92) | 13.8 (0.96) | 193 (0.81) | 12.2 (0.95) |
| 150° C. | 172 (0.79) | 13.9 (0.97) | 172 (0.72) | 12.2 (0.95) |
| 200° C. | 139 (0.64) | 13.7 (0.95) | 130 (0.54) | 11.9 (0.93) |
| 225° C. | 115 (0.53) | 13.1 (0.91) | 76 (0.32) | 9.2 (0.72) |
| 250° C. | 90 (0.41) | 12.1 (0.84) | 29 (0.12) | 5.0 (0.39) |

The parenthesized figures are the ratios to the values measured at room temperature.

To evaluate the water resistance of the composite material obtained in Example 27, the test piece was continuously immersed for 10 days in boiling water. It was then taken out and wiped with a dry cloth to remove adhering water. The water absorption of the test piece as a change in weight was measured. The flexural strength of the immersed test piece was measured at room temperature and 200° C., and compared with that before the immersion treatment. The results are shown in Table 10. The same measurement was made on the test piece of Comparative Example 3. It is seen from Table 10 that the composite material of this invention prepared by using the novel resin of this invention has a low water absorption and a high flexural strength and a high strength retention at high temperatures, thus showing very good heat resistance and water resistance.

TABLE 10

| Test item | Example 27 | | Comparative Example 3 | |
|---|---|---|---|---|
| | Before treatment | After treatment (retention) | Before treatment | After treatment (retention) |
| Water absorption (%) | — | 0.91 | — | 1.56 |
| Flexural strength at room temperature (kg f/mm$^2$) | 224 | 203 (91%) | 239 | 204 (85%) |
| Flexural strength at 200° C. (kg f/mm$^2$) | 140 | 107 (76%) | 130 | 51 (39%) |

(*)The polyglycidyl ether of Example 2 was used.
(**)The polyglycidyl ether of Example 3 was used.
(***)The polyglycidyl ether of Example 5 was used.

EXAMPLES 28 TO 30

To 25 parts of each of the polyglycidyl ether obtained in Examples 2, 3 and 5 was added 6.2 parts of 4,4'-diaminodiphenylsulfone. Furthermore, 30 parts of methyl ethyl ketone was added to form a resin solution. Carbon fibers were impregnated in the resin solution as in Example 27 to form a unidirectionally fiber-reinforced molded article. The dynamic properties of the molded articles obtained in these examples are shown in Table 11.

TABLE 11

| Test item | Measuring temperature | Example 28 (*) | Example 29 () | Example 30 (*) |
|---|---|---|---|---|
| Flexural strength (kg f/mm$^2$) | Room temperature | 220 | 230 | 237 |
| | 200° C. | 139 | 140 | 140 |
| Flexural modulus (10$^3$ kg f/mm$^2$) | Room temperature | 12.6 | 13.0 | 12.9 |
| | 200° C. | 12.6 | 12.9 | 12.3 |

EXAMPLE 31

To 24 parts of the polyglycidyl ether obtained in Example 1 were added 6.2 parts of 4,4'-diaminodiphenylsulfone and 30 parts of acetone to form a solution. Long fibers of aramide fibers (Kepler 49 made by E.I. du Pont de Nemours & Co.; 1000 filaments/1420 denier) were impregnated in the resin solution and then wound up on a drum. The assembly was molded and post-cured in the same way as in Example 27 to obtain a unidirectionally fiber-reinforced molded article having a thickness of 2 mm and a fiber content of 60% by volume. The dynamic properties of the molded article are shown in Table 12.

TABLE 12

| Test item | Measuring temperature | Example 31 |
|---|---|---|
| Flexural strength (kg f/mm$^2$) | Room temperature | 70 |
| | 200° C. | 43 |
| Flexural modulus (10$^3$ kg f/mm$^2$) | Room temperature | 7.3 |
| | 200° C. | 5.0 |

EXAMPLE 32

To 25 parts of the polyglycidyl ether obtained in Example 1 were added 6.2 parts of 3,3'-diaminodiphenylsulfone and 30 parts of acetone to form a solution. Long glass fibers (E glass; 10,000 filaments/20,000 denier) were impregnated in the resin solution and wound up on a drum. The assembly was molded and post-cured in the same way as in Example 27 to obtain a unidirectionally fiber-reinforced molded article having a thickness of 2 mm and a fiber content of 65% by weight. The dynamic properties of the resulting molded article are shown in Table 13.

TABLE 13

| Test item | Measuring temperature | Example 32 |
|---|---|---|
| Flexural strength (kg f/mm$^2$) | Room temperature | 120 |
| | 200° C. | 93 |
| Flexural modulus (10$^3$ kg f/mm$^2$) | Room temperature | 4.6 |
| | 200° C. | 4.3 |

EXAMPLE 33

To 24 parts of the polyglycidyl ether obtained in Example 5 were added 6.2 parts of 4,4'-diaminodiphenylsulfone and 30 parts of acetone to form a resin solution. The solution was mixed with 9 parts of talc powder, and acetone was evaporated. The residue was put in a mold kept at 180° C., and press-cured by a press-molding device. Furthermore, it was maintained for 4 hours in a hot air circulating-type constant temperature vessel kept at 220° C. to postcure it and produce a molded article having a thickness of 2 mm. The dynamic properties of the molded article are shown in Table 14.

TABLE 14

| Test item | Measuring temperature | Example 33 |
|---|---|---|
| Flexural strength (kg f/mm$^2$) | Room temperature | 9.0 |
| | 200° C. | 7.0 |
| Flexural modulus (10$^3$ kg f/mm$^2$) | Room temperature | 0.5 |
| | 200° C. | 0.4 |

What is claimed is:

1. A polyglycidyl ether represented by the following formula (I)

$$R^2 \!\!-\!\!\underset{\underset{OG}{|}}{\overset{\overset{R^1}{|}}{C}}\!\!H\!\!-\!\!\left[\underset{GO}{\overset{R^1}{\phantom{|}}}\!\!-\!\!\underset{\phantom{OG}}{\overset{\overset{R^1}{|}}{C}}\!\!H\!\!-\right]_n\!\!\underset{OG}{\overset{R^2}{\phantom{|}}} \qquad (I)$$

wherein

G represents a hydrogen atom, $$CH_2\!\!-\!\!\underset{O}{\overset{\phantom{|}}{\diagdown\!\!\diagup}}\!\!CHCH_2\!\!- \text{ or } CH_2\!\!-\!\!\underset{O}{\overset{CH_3}{\diagdown\!\!\!\overset{|}{C}\!\!\!\diagup}}\!\!CH_2\!\!-,$$

R$^1$ represents a hydrogen atom, an aliphatic hydrocarbon group having 1 to 10 carbon atoms, an alicyclic hydrocarbon group having 5 to 10 carbon atoms, an aromatic hydrocarbon group having 6 to 10 carbon atoms or a 5- or 6-membered heterocyclic group containing an oxygen or sulfur atom as a hetero atom, provided that the foregoing groups other than the hydrogen atom may be substituted by a halogen atom or the group —OG in which G is as defined, R$^2$ represents a hydrogen atom or the group $$-\!\!\underset{\underset{R^1}{|}}{C}\!\!HOG$$

in which G and R$^1$ are as defined, and n is a positive number up to 10, provided that all groups G, all groups R$^1$ and all groups R$^2$ in the molecule may respectively be identical or different but at least two G groups in the molecule are $$CH_2\!\!-\!\!\underset{O}{\overset{\phantom{|}}{\diagdown\!\!\diagup}}\!\!CHCH_2\!\!- \text{ or } CH_2\!\!-\!\!\underset{O}{\overset{CH_3}{\diagdown\!\!\!\overset{|}{C}\!\!\!\diagup}}\!\!CH_2\!\!-.$$

2. The polyglycidyl ether of claim 1 wherein G in formula (I) is $$CH_2\!\!-\!\!\underset{O}{\overset{\phantom{|}}{\diagdown\!\!\diagup}}\!\!CHCH_2\!\!- \text{ or both } CH_2\!\!-\!\!\underset{O}{\overset{\phantom{|}}{\diagdown\!\!\diagup}}\!\!CHCH_2\!\!-$$

and a hydrogen atom.

3. A process for producing a polyglycidyl ether represented by the following formula (I)

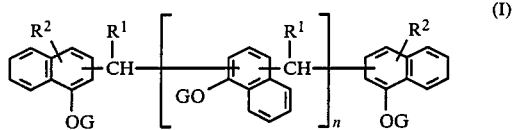

which comprises condensing alpha-naphthol with at least one aldehyde represented by the following formula (II)

wherein $R^3$ represents a hydrogen atom, an aliphatic hydrocarbon group having 1 to 10 carbon atoms, an alicyclic hydrocarbon group having 5 to 10 carbon atoms, an aromatic hydrocarbon group having 6 to 10 carbon atoms, or a 5- or 6-membered heterocyclic group containing an oxygen or sulfur atom as a hetero atom, provided that the foregoing groups other than the hydrogen atom may be substituted by a halogen atom or a hydroxyl group, in the presence of an acid catalyst and optionally in the further presence of an inert reaction medium to form a polyol represented by the following formula (III)

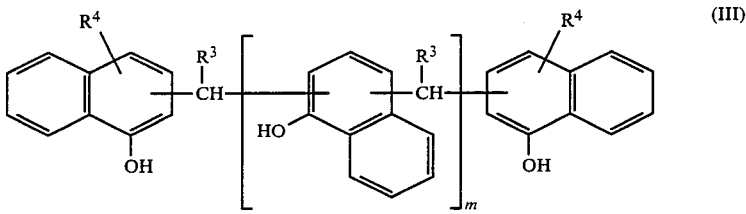

wherein
$R^3$ is as defined,
$R^4$ represents a hydrogen atom or

in which $R^3$ is as defined, and
m is a positive up to 10 number, provided that all $R^3$ groups and all $R^4$ groups may respectively be identical or different,
and thereafter condensing the resulting polyol with an epihalohydrin represented by the following formula (IV)

wherein $R^5$ represents a hydrogen atom or a methyl group, and X represents a halogen atom.

4. The process of claim 3 wherein the condensation reaction between the polyol of formula (III) and the epihalohydrin of formula (IV) is carried out in the presence of an alkali metal hydroxide or an alkaline earth metal hydroxide.

5. The process of claim 3 wherein the condensation reaction between the polyol of formula (III) and the epihalohydrin of formula (IV) is carried out by first subjecting the polyol and the epihalohydrin to ring-opening addition reaction in the presence of a quaternary ammonium salt to form the corresponding polyhalohydrin ether, and thereafter cyclo-condensing the resulting polyhalohydrin ether in the presence of an alkali meal hydroxide or an alkaline earth metal hydroxide.

6. A cured product of the polyglycidylether of formula (I) as defined in claim 1.

7. A composite material comprising a matrix composed of a cured product of the polyglycidyl ether of formula (I) as defined in claim 1.

8. The composite material of claim 7 wherein the filler is a fibrous reinforcing material.

9. The cured product of claim 6 which is characterized by a high char yield when exposed to temperatures of 500° C. or higher and by a strength retention of at least 70% when exposed to a temperature of about 200° C.

10. The polyglycidyl ether of formula (I) according to claim 2 wherein at least one group $R^1$ is hydrogen.

11. The polyglycidyl ether of formula (I) according to claim 2 wherein at least one group $R^1$ is an aliphatic, alicyclic, or aromatic hydrocarbon group or such hydrocarbon group substituted by halogen atom or hydroxy group, and selected from the group consisting of methyl, ethyl, propyl, butyl, pentyl, hexyl, heptyl, octyl, nonyl, decyl, chloromethyl, hydroxyethyl, chloroethyl, propen-1-yl, butene-1-yl, 3-fluoropropen-1-yl, cyclopentyl, cyclohexyl, chlorocyclohexyl, hydroxycyclohexyl, bromocyclohexyl, decalyl, phenyl, hydroxyphenyl, fluorophenyl, bromophenyl, naphthyl and hydroxynaphthyl.

12. The polyglycidyl ether of formula (I) according to claim 2 wherein at least one group $R^1$ is a 5- or 6-membered heterocyclic group selected from the group consisting of furyl, thienyl and pyranyl.

13. The polyglycidyl ether of formula (I) according to claim 1 wherein at least one group $R^1$ is the aliphatic hydrocarbon group, alicyclic hydrocarbon group, aromatic hydrocarbon group or heterocyclic group which is substituted by the group —OG in which G is

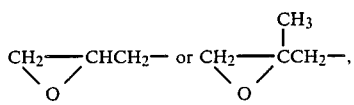

and n is from 1 to 3.

14. The polyglycidyl ether of claim 1 wherein the bridging groups

are located mainly at the ortho- and para-positions to the group —OG of the alpha-naphthol group and when R² is the group

it is located at the ortho-position when the bridging group

is at the para-position and is at the para-position when the bridging group

is at the ortho-position.

15. The polyglycidyl ether of claim 1 wherein R² is a hydrogen atom and wherein there are from 3 to 10 groups of the formula

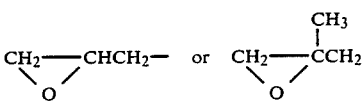

in the molecule.

16. The polyglycidyl ether of claim 1 which has an epoxy equivalent of from about 180 to about 450 g/equivalents and a melting point of about 50° to about 150° C.

17. The process of claim 3 wherein the aldehyde represented by the formula (II) is at least one compound selected from the group consisting of formaldehyde, acetaldehyde, propionaldehyde, butyraldehyde, cyclohexyl aldehyde, benzaldehyde, p-hydroxy-benzaldehyde and p-chlorobenzaldehyde; the acid catalyst is a protonic acid selected from the group consisting of mineral acids, organic sulfonic acids, and organic carboxylic acids; the amount of the catalyst being from about 0.001 to 0.05 mole per mole of the starting alpha-naphthol; the condensation reaction between the alpha-naphthol and aldehyde being at a temperature of about 80° to 250° C.

18. The process of claim 17 wherein the condensation reaction between the alpha-naphthol and the aldehyde is carried out in the presence of an aprotic inert reaction medium selected from the group consisting of toluene, chlorobenzene, dichlorobenzene, nitrobenzene, diphenyl ether, dimethyl ether of ethylene glycol and dimethyl ether of ethylene glycol.

19. The process of claim 4 wherein the alkali metal hydroxide or alkaline earth metal hydroxide is used in a proportion of 0.8 to 1.2 moles per hydroxyl equivalent of the polyol of formula (III) and the epihalohydrin of formula (IV) is used in an amount of 5 to 20 moles per hydroxyl equivalent of the polyol of formula (III) and the condensation reaction between the polyol of formula (III) and the epihalohydrin of formula (IV) is carried out at a temperature of from about 60° C. to about 120° C.

20. The process of claim 5 wherein the quaternary ammonium salt of formula (V) is tetramethyl ammonium chloride, tetraethyl ammonium bromide or trimethylbenzyl ammonium chloride and is used in a catalytic amount of from about 0.001 to 0.2 mole per hydroxyl equivalent of the polyol of formula (III) and the epihalohydrin of formula (IV) is used in a proportion of 5 to 20 moles per hydroxyl equivalent of the polyol of formula (III) and the condensation reaction between the polyol of formula (III) and the epihalohydrin of formula (IV) is carried out at a temperature of from about 70° C. to about 150° C.; and the cyclocondensation of the resulting polyhalohydrin is at a temperature of from about 60° C. to about 120° C.

* * * * *

UNITED STATES PATENT AND TRADEMARK OFFICE
CERTIFICATE OF CORRECTION

PATENT NO. : 4,551,508
DATED : November 5, 1985
INVENTOR(S) : TAKANORI URASAKI

It is certified that error appears in the above-identified patent and that said Letters Patent is hereby corrected as shown below:

IN THE CLAIMS

Claim 3, line 26, (column 25, line 47),
delete "m is a positive up to 10 number",
insert --m is a positive number up to 10--.

Signed and Sealed this

Twenty-ninth Day of July 1986

[SEAL]

Attest:

DONALD J. QUIGG

Attesting Officer

Commissioner of Patents and Trademarks